May 13, 1975 A. B. COOK Plant Pat. 3,718

STRAWBERRY PLANT

Filed Nov. 15, 1973

United States Patent

Plant Pat. 3,718

Patented May 13, 1975

3,718

STRAWBERRY PLANT

Albert B. Cook, Grandview, Ind., assignor to Herschel L. Boll, Champaign, Ill.

Filed Nov. 15, 1973, Ser. No. 416,295

Int. Cl. A01h *5/03*

U.S. Cl. Plt.—49 1 Claim

My invention relates to a new and distinct variety of strawberry plant. It is the result of a cross of [(Canall × Twentieth Century) × self] × Streamliner, made by me in 1964, at Grandview, Ind.

Since my discovery of the original plant, I have asexually reproduced a large number of plants from the original mother plant by rooted runners.

My object in the asexual propagation of the original mother plant was to determine the characteristics of the plant and of its fruit by the testing of a large number of plants. The distinguishing features of my new variety have proved to be permanent. My new variety has proved itself to have unusual possibilities because of its everbearing habit of growth; its high productivity; its vigorous growth; its continuous bearing of fruit from June until freezing weather; its continuous production of new flower stems, enabling one to pick some large primary berries at any time during the bearing season; and its large, conic, orange-red fruit.

Figure 1:
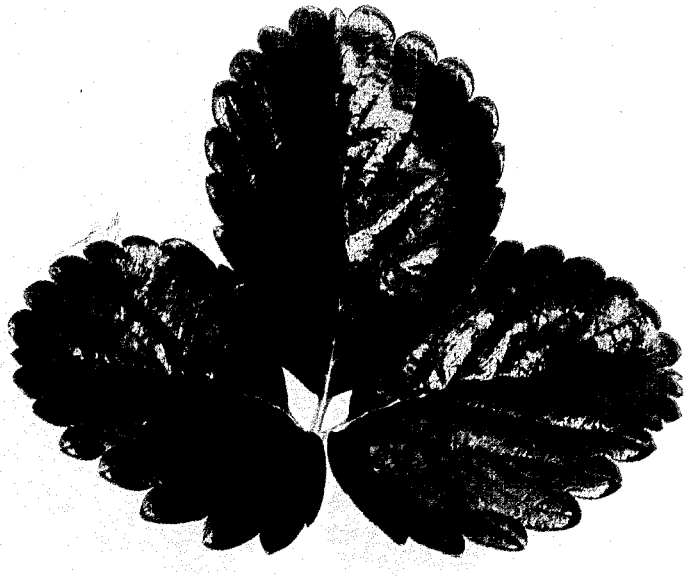
FIG. 1 shows a typical leaf in full color.
Figure 2:
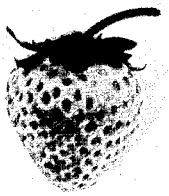
FIG. 2 is a berry of typical shape.
Figure 3:
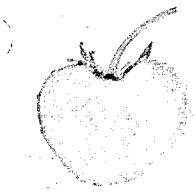
FIG. 3 shows a typical central longitudinal section of a berry.

In general, the distinct and new variety of strawberry plant, which is the subject of my invention and discovery, is characterized by its everbearing habit of growth; by its high productivity; by its vigorous growth; by its continuous bearing of fruit from June until freezing weather; by its continuous production of new flower stems, enabling one to pick some large primary berries (in southwestern Michigan, up to 1¾ inches in diameter, and averaging about 1¼ to 1½ inches) at any time during the bearing season; and by its large, conic, orange-red fruit. These characteristics I now refer to in greater detail. Color plate references are according to Color Standards and Color Nomenclature by Robert Ridgway.

Under the conditions at Grandview, Ind., and at Champaign, Ill., my new variety of plant is everbearing and high in productivity, largely because it bears continuously from June until freezing weather. It is adapted farther south in the Midwest than most other everbearers. It is even better adapted in southwestern Michigan. The plants are vigorous, and are short to medium in height. They produce a medium number of runners (about 5 to 6 per plant) for an everbearer, which is less than either Sonjana (Plant Pat. 1,691) or Gem.

The leaves are slightly dark green in color, or are approximately Cedar Green (Plate VI), or varying from Forest Green (Plate XVII) to Cedar Green (Plate VI)

to Cerro Green (Plate V), depending mainly on soil fertility, but also depending on other soil conditions, exposure, and weather and climatic conditions. The leaves are medium in size, glossy, slightly cupped, and slightly smoother than average. The terminal leaflet overlaps the lateral leaflets. The flowers are perfect. The date of the first blossoms in 1972 at Champaign, Ill., was May 6.

At Grandview, Ind., and at Champaign, Ill., my new variety of strawberry plant begins to mature its fruit in midseason (at about the same time as Catskill, but Catskill is a June-bearer), and bears continuously until freezing weather. The date of the first picking in 1972 at Champaign, Ill., was June 3. New flower stems appear continuously, enabling one to pick some large primary berries at any time during the bearing season. The berries are well formed throughout the bearing season.

The fruit is orange-red (it is medium dark red for Locke Lake Ruby (Plant Pat. 2,429), and deep red for Sonjana and Gem), or is approximately Scarlet-Red (Plate I), or varying from Scarlet (Plate I) to Scarlet-Red (Plate I) to Spectrum Red (Plate I), depending mainly on exposure, but also depending on soil, weather, and climatic conditions. The fruit is large—larger in southwestern Michigan. It is medium in size for Sonjana, and small to medium for Gem. The fruit of my new variety is conic in shape, while it is heart-shaped for Locke Lake Ruby, blunt conic for Sonjana, and short wedge to oblate for Gem. It is slightly glossy and firm.

The calyx is medium in size, and is sunken. The achenes are about flush with the surface to slightly raised, and are yellow to red depending on exposure.

Under the conditions existing where I have reproduced and tested my new variety of strawberry plant, the flesh of the berry is white to light orange-red, but it is red with a whitish area for Locke Lake Ruby. The berry has a soft core, which is usually removed as the calyx is removed. Locke Lake Ruby is solid inside. The fruit is relatively sweet (it is acid for Gem), and is medium in flavor.

The strawberry above described, and the plant producing it, of course, may vary in slight details, depending on soil, weather, and climatic conditions.

What I claim is:

1. A new and distinct variety of strawberry plant substantially as herein shown and described, characterized by its everbearing habit of growth; by its high productivity; by its vigorous growth; by its continuous bearing of fruit from June until freezing weather; by its continuous production of new flower stems, enabling one to pick some large primary berries at any time during the bearing season; and by its large, conic, orange-red fruit.

References Cited

UNITED STATES PATENTS

| | | | | |
|---|---|---|---|---|
| P.P. | 1,691 | 3/1958 | Hummel | Plants—49 |
| P.P. | 2,429 | 7/1964 | Brunnen | Plants—49 |

ROBERT E. BAGWILL, Primary Examiner